United States Patent [19]
Wagner

[11] Patent Number: 5,620,467
[45] Date of Patent: Apr. 15, 1997

[54] IMPLANTABLE ATRIAL DEFIBRILLATOR HAVING CARDIOVERTING OUTPUT VOLTAGE LIMITING FOR SIMULATING LARGER STORAGE CAPACITORS

[75] Inventor: Darrell O. Wagner, Gold Bar, Wash.

[73] Assignee: InControl, Inc., Redmond, Wash.

[21] Appl. No.: 541,682

[22] Filed: Oct. 10, 1995

[51] Int. Cl.$^6$ .................................................. A61N 1/00
[52] U.S. Cl. ................................................. 607/5; 607/63
[58] Field of Search .................................. 607/9, 6, 7, 8, 607/12, 34, 63

[56] References Cited

U.S. PATENT DOCUMENTS 5,318,591  6/1994  Causey, III et al. ........................ 607/7

Primary Examiner—William E. Kamm
Assistant Examiner—Scott M. Getzow
Attorney, Agent, or Firm—Richard O. Gray, Jr.

[57] ABSTRACT

An implantable atrial defibrillator includes a storage capacitor for storing electrical energy. A switch discharges at least a portion of the stored energy into a patient's heart as a discharge voltage and a charger charges the storage capacitor with the stored energy to a peak voltage. A voltage limiter precludes the discharge voltage from exceeding a voltage limit during capacitor discharge to permit a reduced applied cardioverting voltage with a lengthened discharge time. The voltage limit is a substantially constant fraction of the peak voltage.

5 Claims, 2 Drawing Sheets

IMPLANTABLE ATRIAL DEFIBRILLATOR HAVING CARDIOVERTING OUTPUT VOLTAGE LIMITING FOR SIMULATING LARGER STORAGE CAPACITORS

BACKGROUND OF THE INVENTION

The present invention generally relates to an automatic implantable atrial defibrillator for delivering cardioverting or defibrillating voltage to the atria of a patient and which is capable of providing effective cardioversion with reduced discomfort to the patient. The present invention is particularly directed to such an atrial defibrillator which includes a cardioverting output voltage limiter for simulating output voltage waveforms provided by storage capacitors of greater capacity than that actually delivering the cardioverting voltage.

Atrial fibrillation is probably the most common cardiac arrhythmia. Although it is not usually a life threatening arrhythmia, it is associated with strokes thought to be caused by blood clots forming in areas of stagnate blood flow as a result of prolonged atrial fibrillation. Patients afflicted with atrial fibrillation generally experience palpitations of the heart and reduced cardiac output. This often leads to dizziness or, in extreme cases, to loss of consciousness.

Atrial fibrillation is often corrected by external defibrillation of the type well known in the art. This treatment involves applying a relatively large quantity of electrical energy to the heart with external skin surface electrodes. The energy is applied in synchronism with a detected R wave (electrical activation) of the heart. The treatment is very painful and can necessitate hospitalization for as many as a few days. Unfortunately, most often, it only provides temporary relief, lasting but a few weeks.

Drugs are available for reducing the incidents of atrial fibrillation. However, such drugs have many side effects. Also, many patients are resistant to them which greatly reduces their therapeutic effect.

In order to negate the need for external defibrillation and drug therapy, implantable atrial defibrillators have been proposed to provide relief for patients suffering from this cardiac arrhythmia. Two such defibrillators, although represented as being implantable, were not fully automatic, requiring human interaction for cardioverting or defibrillating the heart. Both of these defibrillators required the patient to recognize the symptoms of atrial fibrillation. One defibrillator required a visit to a physician for activating the defibrillator. The other defibrillator required the patient to activate the defibrillator with a magnet from external to the patient's skin.

It is preferable that an implantable cardiac device, such as an atrial defibrillator, be truly automatic. In order for an implantable atrial defibrillator to be truly automatic, it must be able to accurately detect atrial fibrillation and then safely apply cardioverting voltage to the atria to convert the same to normal sinus rhythm (NSR).

Detection of atrial fibrillation is a two-part process. First, an atrial defibrillator must be able to sense activity of the heart, such as atrial activity. One atrial defibrillator having such capability is fully disclosed in Jin et al., U.S. Pat. No. 5,267,559 which issued on Dec. 7, 1993 for ATRIAL DEFIBRILLATOR AND METHOD FOR PROVIDING ATRIAL SENSING and which is assigned to the assignee of the present invention and incorporated herein by reference.

After heart activity, such as atrial activity, is sensed, an atrial fibrillation detector then must determine if the sensed heart activity satisfies a fibrillation criteria. One such detector is fully disclosed in co-pending U.S. application Ser. No. 08/233,251, filed Apr. 26, 1994 in the names of Harley G. White and Joseph M. Bocek for SELECTIVE CARDIAC ACTIVITY ANALYSIS ATRIAL FIBRILLATION DETECTION SYSTEM AND METHOD AND ATRIAL DEFIBRILLATOR UTILIZING SAME. Another such detector is fully disclosed in co-pending U.S. application Ser. No. 08/278,055, filed Jul. 20, 1994 in the names of Jaeho Kim and Harley G. White for SYSTEM AND METHOD FOR REDUCING FALSE POSITIVES IN ATRIAL FIBRILLATION DETECTION. Both of the aforementioned co-pending applications are assigned to the assignee of the present invention and incorporated herein by reference.

Each of the aforementioned co-pending applications discloses a preferred embodiment of an atrial fibrillation detector wherein atrial cardiac events are detected from sensed atrial activity. Further, each of these preferred embodiments includes ventricular activity sensing and detection of R waves. Atrial fibrillation is detected from atrial activity occurring between detected R waves.

Once atrial fibrillation is detected, it is then necessary to apply a cardioverting voltage pulse to the atria to return the heart to NSR. To that end, a storage capacitor is charged to a voltage and then discharged to apply the cardioverting voltage to the heart. To assure that the cardioverting voltage is safely applied to the atria, it is preferred that the capacitor is discharged in synchronism with a detected R wave. To that end, co-pending U.S. application Ser. No. 08/259,476 filed Jun. 14, 1994 in the name of Harley G. White for CARDIOVERSION SYNCHRONIZATION SYSTEM AND METHOD FOR AN ATRIAL DEFIBRILLATOR, which is assigned to the assignee of the present invention and incorporated herein by reference discloses a synchronization system which includes two ventricular sense channels and requires that an R wave be sensed in both channels before the voltage may be applied. In addition, other synchronization criteria may be required to be satisfied such as a minimum interval criteria as described, for example, in Adams, et al., U.S. Pat. No. 5,207,219, which issued on May 4, 1993 for ATRIAL DEFIBRILLATOR AND METHOD FOR PROVIDING INTERVAL TIMING PRIOR TO CARDIOVERSION, and which is assigned to the assignee of the present invention and incorporated herein by reference.

Hence, as can be seen from the foregoing, an automatic atrial defibrillator must reliably sense heart activity, reliably detect the need for cardioversion, and safely apply cardioverting voltage to the atria of the patient's heart. In order to provide reasonable assurance that the cardioverting voltage will indeed successfully cardiovert the atria, the voltage applied should have a peak value above a determined minimum peak value required to effectively cardiovert the atria. That voltage level is commonly referred to as the defibrillation threshold.

The peak voltage required to effectively cardiovert increases as the capacitor discharge time or pulse width decreases. The capacitor discharge rate increases (resulting in shorter capacitor discharge times) as the capacitor capacitance decreases. Hence, larger capacitances can discharge over a longer time period than smaller capacitances. Also as a result, larger capacitances require a lower peak voltage to effectively cardiovert.

Since patients suffering from atrial fibrillation will be conscious during cardioversion (unlike patients suffering from ventricular fibrillation), perceived discomfort or pain caused by the cardioversion becomes an issue. Obviously, the less discomfort a patient experiences as a result of cardioversion the better.

Discomfort or pain resulting from cardioversion is a nervous system response to the discharged voltage. The physiologic basis for this is that nerve tissue has a much faster membrane time constant than cardiac muscle. Therefore, shorter and higher peak voltage discharges create more pain or discomfort than do longer and lower peak voltage discharges.

The logical conclusion from the foregoing would be to use as high a capacitance as possible to cardiovert the atria. This would result in the longest discharge time, the lowest required peak voltage, and the least discomfort for successful cardioversion. Unfortunately, the size of an implantable device is also of importance. Higher capacitance values require capacitors of larger size. Obviously, a point is reached where capacitor size becomes impractical.

For atrial defibrillation, it has been determined that for many patients, a capacitor having a capacitance in the range of 70 to 100 microfarads ($\mu F$) and more particularly 80 $\mu F$ with a total discharge time of six milliseconds is a suitable choice in terms of voltage threshold and capacitor size. Some patients, however, may experience discomfort at their voltage threshold. For these patients, a longer discharge time and lower voltage threshold would be more desirable. Unfortunately, this would require a higher storage capacitance value and hence a larger sized capacitor which may not be practical.

The present invention provides an elegant solution to this problem. In accordance with its broader objectives, the present invention permits a capacitor to be discharged for a period of time which is longer than it normally would be discharged. It also, at the same time, permits a lower voltage to be applied to the patient's heart to achieve successful cardioversion. In doing so, the capacitance value, and hence the capacitance size, need not be increased.

SUMMARY OF THE INVENTION

The present invention provides, in an implantable atrial defibrillator which includes a storage capacitor for storing electrical energy, switch means for discharging at least a portion of the stored energy into a patient's heart as a discharge voltage and charging means for charging the storage capacitor with the stored energy to a peak voltage, the improvement comprising limiting means for precluding the discharge voltage from exceeding a voltage limit, the voltage limit being a substantially constant fraction of the peak voltage.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
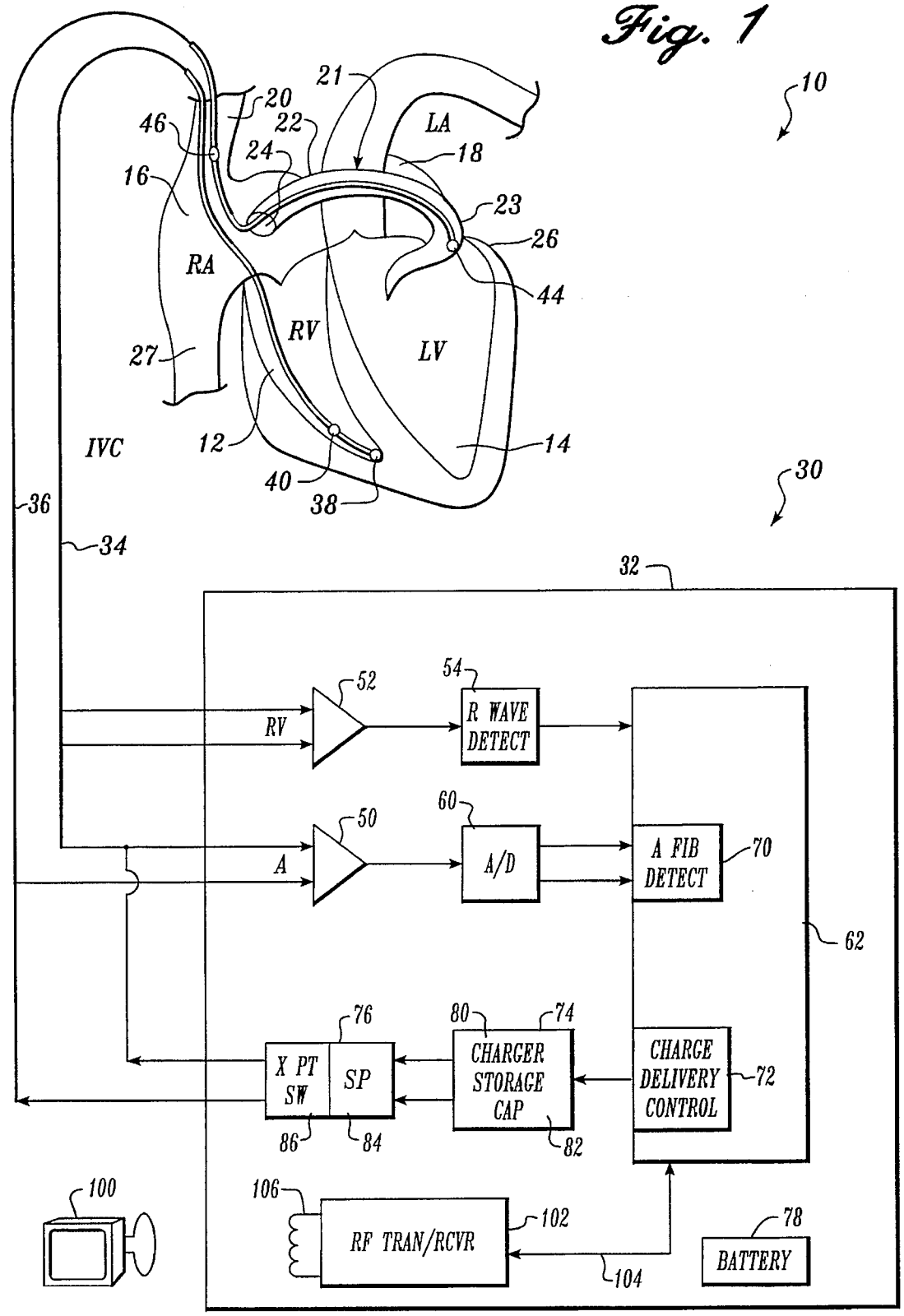
FIG. 1 is a schematic block diagram of a fully implantable atrial defibrillator embodying the present invention for applying defibrillating voltage to the atria of a human heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "electrical activations" denotes R waves of the heart cardiac cycle which are depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16, and then into the right ventricle 12.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16.

The first electrode 44 together with the second electrode 46 provide bi-polar sensing of heart activity in the atria 16 and 18. The first electrode 44 and the second electrode 46 further provide for the delivery of defibrillating electrical energy or voltage to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10.

Within the enclosure 32, the atrial defibrillator 30 includes a first sense amplifier 50, a second sense amplifier 52, and an R wave detector 54. The first sense amplifier 50 forms a first sensing means which, together with the first electrode 44 and second electrode 46 of the second lead 36 to which it is coupled detects atrial activity of the heart. The second sense amplifier 52 and the R wave detector 54 form a second sensing means which together with the first lead 34 to which sense amplifier 52 is coupled, sense ventricular activations of the right ventricle 12.

The output of the first sense amplifier 50 is coupled to an analog to digital converter 60 which converts the analog signal representative of the sensed atrial activity of the heart to digital samples for further processing in a manner to be described hereinafter. The output of the second sense amplifier 52 is coupled to the R wave detector 54. The R wave detector 54 is of the type well known in the art which provides an output pulse upon the occurrence of an R wave being sensed during a cardiac cycle of the heart.

The enclosure 32 of the atrial defibrillator 30 further includes a microprocessor 62. The microprocessor 62 is preferably implemented in a manner as disclosed in the aforementioned copending U.S. applications, Ser. Nos. 08/233,251 and 08/278,055 to form an atrial fibrillation detector 70, and as disclosed in U.S. Pat. No. 5,251,624, which issued on Oct. 12, 1993, to form a charge delivery and energy control stage 72. U.S. Pat. No. 5,251,624 is assigned to the assignee of the present invention and incorporated herein by reference.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and conveys the date to the memory over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, such as defibrillation peak voltage levels into stage 72, or for receiving operating commands, the microprocessor 62 receives the programmable operating parameters and operating commands from an external controller 100 which is external to the skin of the patient and under the control of an operator, such as a physician. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters and operating commands from the external controller 100 which the receiver/transmitter 102 then conveys to the microprocessor 62 for storage in interval memory.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures and for transmitting data to the external controller 100 from the implanted enclosure 32. One such communication system is disclosed, for example, in U.S. Pat. No. 5,342,408 which is also issued to the assignee of the present invention and incorporated herein by reference.

To complete the identification of the various structural elements within the enclosure 32, the atrial defibrillator 30 further includes a charger and storage capacitor circuit 74 of the type disclosed in the aforementioned U.S. Pat. No. 5,251,624 which includes a charger 80 for charging a storage capacitor 82 with energy to a peak voltage. The atrial defibrillator 30 further includes a discharge circuit 76. The discharge circuit 76 includes a series-pass circuit 84 embodying the present invention and a crosspoint switch 86 as disclosed in the aforementioned U.S. Pat. No. 5,251,624 for discharging the storage capacitor 82 within circuit 74 in accordance with the present invention to provide a controlled voltage discharge of reduced voltage and increased pulse width to reduce patient discomfort during cardioversion of the atria of the heart. The discharge circuit 76 is coupled to the first electrode 44 and the second electrode 46 of the second lead 36 for applying the cardioverting or defibrillating voltage to the atria. Lastly, the defibrillator 30 includes a depletable power source 78, such a lithium battery, for providing power to the electrical components of the atrial defibrillator 30.

When the atrial defibrillator 30 is operative in its normal operating mode, the atrial fibrillation detector 70, sense amplifier 50, and the analog to digital converter 60 are preferably enabled at predetermined times as disclosed in a copending U.S. application Ser. No. 08/232,767, entitled AN IMPLANTABLE ATRIAL DEFIBRILLATOR HAVING AN INTERMITTENTLY ACTIVATED FIBRILLATION DETECTOR, filed Apr. 25, 1994, which application is assigned to the assignee of the present invention and incorporated herein by reference. If the atrial fibrillation detector 70 determines that the atria 16 and 18 are in fibrillation and thus in need of cardioversion, the charge delivery control 72 causes the charger 80 to charge the storage capacitor 82 with energy to a peak voltage level above the patient's threshold. Then, when synchronization criteria are met as disclosed in the aforementioned U.S. Pat. No. 5,207,219 and application Ser. No. 08/259,476 for example, the charge delivery control 72 cause the discharge circuit 76 to discharge some of the voltage on capacitor 82 into electrodes 44 and 46 for cardioverting the atria.

In accordance with the present invention, the discharge pulse width is longer than would normally be the case for the capacitance value of capacitor 82. This is made possible by the series-pass circuit 84 which precludes the discharge voltage from exceeding a voltage limit which is a substantially constant fraction of the peak voltage. More specifically, and as an example, the capacitor 82, which may have a capacitance of 80 µF, is charged to a peak voltage necessary to satisfy the threshold for a 3 millisecond by 3 millisecond biphasic discharge waveform. However, the capacitor 82 is preferably discharged with a six millisecond by six millisecond biphasic waveform while the series-pass circuit 84 precludes the discharge voltage from exceeding a voltage limit which is three-fourths the peak voltage. In doing so, a sufficient but lower voltage cardioverts the atria with twice the pulse width. As a result, the patient experiences reduced discomfort as if a capacitance of 160 µF were used.

Figure 3:
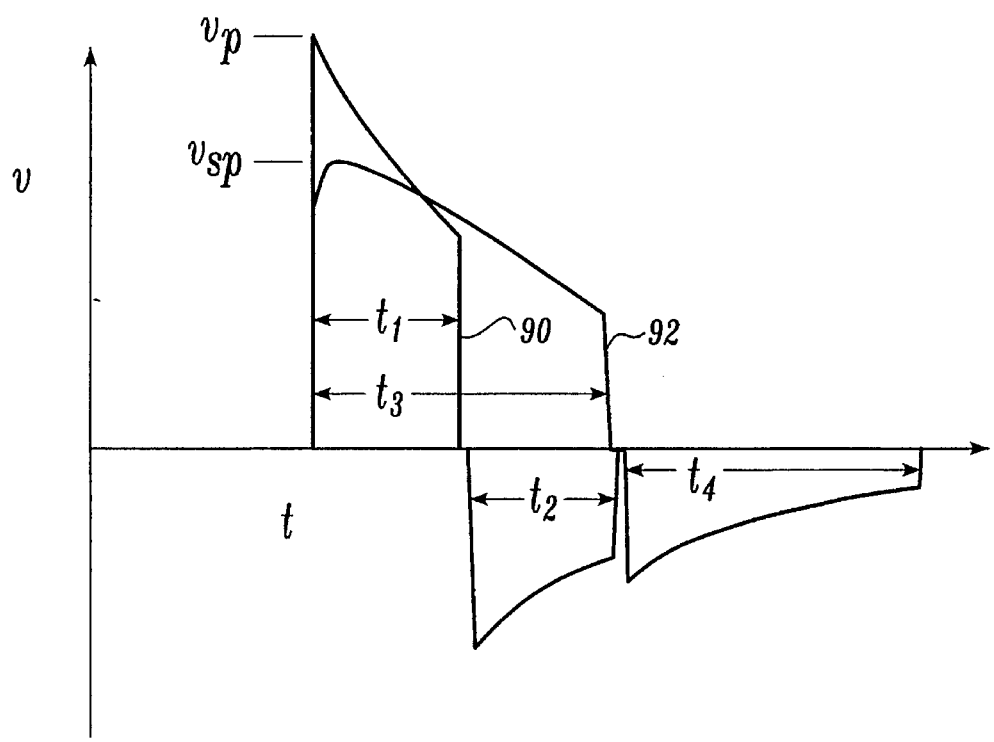
FIG. 3 illustrates superposed voltage versus time defibrillating voltage waveforms for illustrating principal aspects of the present invention.

FIG. 3 illustrates the differences in the two discharge voltage waveforms when using a storage capacitor of 80 µF. Waveform 90 is a three millisecond (3 ms) by three millisecond (3 ms) biphasic waveform normally produced using an 80 µF capacitor. Hence, both time periods or phases $t_1$ and $t_2$ are three milliseconds. The peak voltage Vp is the peak discharge voltage necessary to exceed the patient's threshold using an 80 µF capacitor and a 3 ms by 3 ms biphasic discharge waveform.

Waveform 92 results when using the series-pass circuit 84 embodying the present invention. The capacitor 82 is still charged to Vp. However, the series-pass circuit precludes the discharge voltage from exceeding a voltage limit Vsp which is a fraction of Vp and sufficient to exceed the patient's threshold when using a biphasic discharge waveform longer than 3 ms by 3 ms. For example, as illustrated in FIG. 3, waveform 92 is a 6 ms by 6 ms biphasic waveform. As a result, the time periods or phases $t_3$ and $t_4$ are six milliseconds and made possible because the series-pass circuit causes the capacitor to be discharged more slowly. More specifically, with a 6 ms by 6 ms biphasic discharge waveform 92, Vsp is preferably three-fourths of Vp. This (Vsp) is sufficient voltage to exceed the patient's threshold with a 6 ms by 6 ms biphasic discharge waveform.

As will be appreciated by those skilled in the art, the series-pass circuit 84 forms a voltage limiter which allows the storage capacitor 82 to appear as if it were of greater capacitance. In the example above, the 80 µF capacitor can be made to appear as a 160 µF capacitor. This reduces the patient's defibrillation threshold voltage by permitting capacitor discharge over a longer discharge time.

Figure 2:
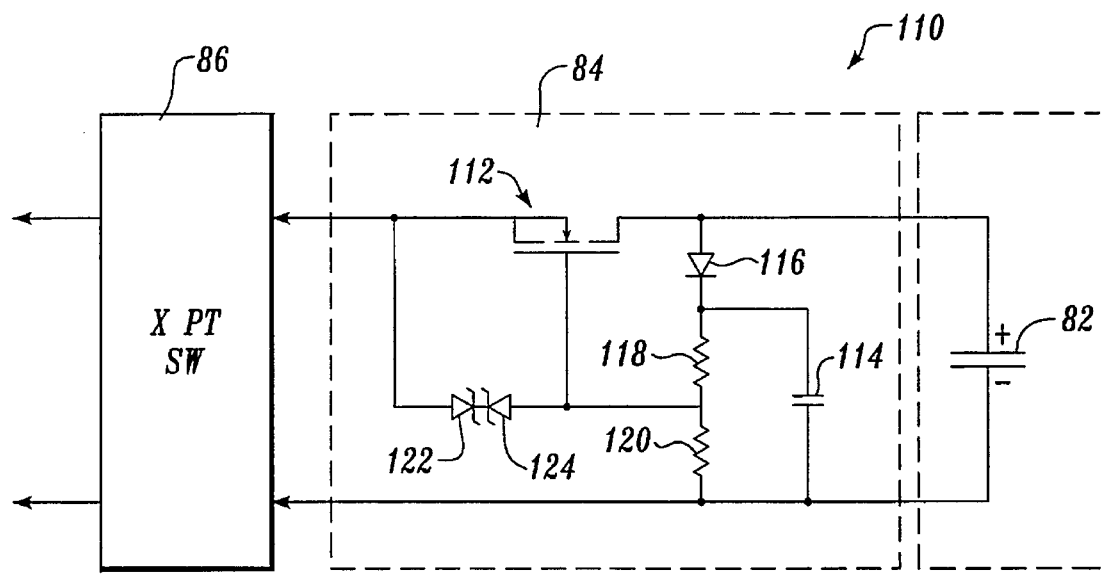
FIG. 2 is a schematic diagram of a preferred embodiment of the present invention.

Referring now to FIG. 2, it illustrates a more detailed schematic diagram of a voltage limiter 110 in the form of a series-pass circuit 84 embodying the present invention. The series-pass circuit 84 is coupled between the storage capacitor 82 and the crosspoint switch 86. The series-pass circuit includes a metal-oxide semiconductor field-effect transistor (MOS FET) 112, capacitor 114, diode 116, resistors 118 and 120 and zener diodes 122 and 124.

Capacitor 114 charges through diode 116 to the voltage level (Vp) on the storage capacitor 82. Resistors 118 and 120 set the fraction of Vp to limit the discharge voltage to below Vsp. Resistors 118 and 120 are preferably high in resistance, each greater than one megohm. Capacitor 114 preferably has a capacitance between 0.01 and 0.10 µF. This combination provides a long enough time constant sufficient to maintain the desired fraction of Vp constant during the capacitor discharge time. The high impedance also coacts with the internal capacitance of FET 112 to smooth the delivered voltage waveform.

The voltage at the source of FET 112 will be held at a level equal to the gate voltage minus the gate-to-source voltage. The source voltage is maintained until the voltage level at the drain drops below the gate voltage. At this point, the series-pass circuits terminates limiting and the output waveform follows its normal time constant shape. The zener diodes 122 and 124 are employed to protect the gate of FET 112 from excessive voltage levels.

While a particular embodiment of the present invention has been shown and described herein, modifications may be made. For example, the principles of the present invention apply as well to monophasic discharge waveforms and other values of storage capacitance. Hence, it is therefore intend to cover in the appended claims, all such changes and modifications which fall within the true spirit and scope of the invention.

What is claimed is:

1. In an implantable atrial defibrillator which includes a storage capacitor for storing electrical energy, switch means for discharging at least a portion of the stored energy into a patient's heart as a discharge voltage and charging means for charging the storage capacitor with the stored energy to a peak pre-discharge voltage, the improvement comprising limiting means for precluding the discharge voltage from exceeding a voltage limit, the voltage limit being a substantially constant fraction of the peak pre-discharge voltage.

2. In an implantable atrial defibrillator which includes a storage capacitor for storing electrical energy switch means for discharging at least a portion of the stored energy into a patient's heart as a discharge voltage and charging means for charging the storage capacitor with the stored energy to a peak voltage, the improvement comprising limiting means including a series-pass circuit for precluding the discharge voltage from exceeding a voltage limit, the voltage limit being a substantially constant fraction of the peak voltage.

3. A defibrillator as defined in claim 2 wherein the limiting means includes means establishing the substantially constant fraction at about three-fourths.

4. A defibrillator as defined in claim 2 wherein the limiting means is coupled between the storage capacitor and the switch means.

5. In an implantable atrial defibrillator which includes a storage capacitor for storing electrical energy, switch means for discharging at least a portion of the stored energy into a patient's heart as a discharge voltage and charging means for charging the storage capacitor with the stored energy to a peak voltage, the improvement comprising a series-pass circuit for precluding the discharge voltage from exceeding a voltage limit.

\* \* \* \* \*